(12) United States Patent
Rogers

(10) Patent No.: US 9,592,314 B2
(45) Date of Patent: Mar. 14, 2017

(54) DISPOSABLE AND SCENTED PAD

(71) Applicant: Renardo Rogers, Calumet City, IL (US)

(72) Inventor: Renardo Rogers, Calumet City, IL (US)

(*) Notice: Subject to any disclaimer, the term of this patent is extended or adjusted under 35 U.S.C. 154(b) by 0 days.

(21) Appl. No.: 14/618,412

(22) Filed: Feb. 10, 2015

(65) Prior Publication Data

US 2015/0224217 A1   Aug. 13, 2015

Related U.S. Application Data

(60) Provisional application No. 61/938,822, filed on Feb. 12, 2014.

(51) Int. Cl.
*A61L 9/12* (2006.01)
*A47G 9/00* (2006.01)
*A61L 9/014* (2006.01)
*A47C 31/00* (2006.01)
*A47C 31/10* (2006.01)

(52) U.S. Cl.
CPC ............. *A61L 9/12* (2013.01); *A47C 31/005* (2013.01); *A47C 31/105* (2013.01); *A47G 9/007* (2013.01); *A61L 9/014* (2013.01)

(58) Field of Classification Search
CPC ... A61L 9/015; A61L 9/12; A61L 9/04; A61L 9/014; A61L 9/01; A47G 9/0007; A47C 31/005; A47C 31/10; A47C 31/105

USPC ..................................................... 239/53–56
See application file for complete search history.

(56) References Cited

U.S. PATENT DOCUMENTS

| 3,382,509 | A | | 5/1968 | Hellmuth | |
|---|---|---|---|---|---|
| 3,623,659 | A | * | 11/1971 | Maierson | B01J 13/025 239/56 |
| 4,356,969 | A | * | 11/1982 | Obermayer | A01M 1/2044 239/56 |
| 6,430,764 | B1 | | 8/2002 | Peters | |
| 2002/0095726 | A1 | | 7/2002 | Michetti | |
| 2007/0094794 | A1 | | 5/2007 | Ellis | |
| 2009/0173425 | A1 | * | 7/2009 | Sammons | A61L 9/042 156/60 |
| 2012/0209058 | A1 | | 8/2012 | Soroush | |
| 2012/0227183 | A1 | | 9/2012 | Muskelly | |

* cited by examiner

*Primary Examiner* — Christopher Kim
(74) *Attorney, Agent, or Firm* — Global Intellectual Property Agency, LLC; Daniel Boudwin

(57) ABSTRACT

A scented and disposable pad having a plurality of layers including a first layer composed of an absorbent material, a second layer that is a gel layer, and a third layer that is a waterproof layer. The gel layer can be embedded with a fragrance in order to provide a pleasing scent to the user. The pad can be placed underneath one's sheet in between the sheet and the mattress of the user. Alternatively, the pad can be placed between a pillow case and a pillow to provide a soothing scent for relaxation and sleep while laying down. At least one layer is embedded with scented micro beads, wherein the scent can include vanilla, lavender, and other scents to promote sleep and relaxation.

9 Claims, 1 Drawing Sheet

DISPOSABLE AND SCENTED PAD

CROSS REFERENCE TO RELATED APPLICATION

This application claims the benefit of U.S. Provisional Application No. 61/938,822 filed on Feb. 11, 2014. The above identified patent application is herein incorporated by reference in its entirety to provide continuity of disclosure.

BACKGROUND OF THE INVENTION

Field of the Invention

The present invention relates to a disposable and scented pad. More specifically the invention relates to disposable and scented pad that can be utilized with a mattress and a pillow, wherein the invention can be embedded with a fragrance, scent, aromatherapy oil, medicinal scents and/or essential oils in order to emit a pleasing scent therefrom to aid with sleep, relaxation and increased mood.

It can be quite difficult to get a good night sleep, individuals often use sleep aids in order to get rest. Others employ the use of candles in order to emit a pleasing scent, however candles can be dangerous if left unattended and sleep aids are not always safe alternatives to falling asleep. Further, having pleasing smelling sheets can be an essential aspect of one's home and one may resort to placing soaps on a pillow in order to provide a pleasing scent thereto. However, this can be ineffective and may only last for a short period of time.

Description of the Prior Art

Devices have been disclosed in the prior art that relate to disposable and/or scented mattress pads. These include devices that have been patented and published in patent application publications. These devices generally relate to disposable and/or scented mattress pads. The following is a list of devices deemed most relevant to the present disclosure, which are herein described for the purposes of highlighting and differentiating the unique aspects of the present invention, and further highlighting the drawbacks existing in the prior art.

Specifically, U.S. Publication No. 2007/0094794 to Ellis discloses a scented disposable bed liner and pillow liner that provides a disposable sheet of non-woven fabric that is adapted to fit over a bed mattress, wherein the device can include a fragrant powder or liquid applied thereto. The present invention however, provides a scented and disposable pad comprising a plurality of layers and can be embedded with medicinal scents, such as menthol, among others.

U.S. Publication No. 2012/0227183 to Muskelly describes a disposable, scented and fitted mattress cover having a disposable substrate, wherein a fragrance can be applied to the substrate in order to emit a scent when secured to a mattress. The present invention however, can be utilized with a mattress as well as a pillow, whereby the user can place the invention beneath a pillow case in order to have greater access to the scent embedded therein.

U.S. Publication No. 2012/0209058 to Arasi discloses a therapeutic pillow having aromatic materials such as lavender, sandalwood and the like in order to relieve stress and elevate a person's mood while stimulating the brain and promoting relaxation. The present invention provides a pad having a plurality of layers including a waterproof layer, a gel layer, and a soft fabric layer in order to provide comfort to the individual while sleeping thereon.

U.S. Pat. No. 6,430,764 to Peters discloses an herbal scented pillow for soothing the user, wherein the device provides herbal aromas. The user can place a scent emitting substance onto provided pouch member, wherein the pouch member can be secured inside the pillow portion. Still, the present invention provides a pad for a mattress or pillow having a plurality of layers, wherein at least one layer can be embedded with a fragrance.

U.S. Publication No. 2002/0095726 provides a scented bed linen that can emit a pleasant scent throughout a bedroom. The bed linen offers a plurality of pockets that can be affixed to the bed linen having odor emitting members inserted therein. However, the present invention provides a scented and disposable pad comprising a plurality of layers, wherein the user can place the invention onto various areas of a bed such as underneath a mattress, bed sheet or in between a pillow and a pillow cover.

U.S. Pat. No. 3,382,509 to Hellmuth allows for a permeable pillow case having filling therein, wherein the filling can be mixed herbs, oils, chamomile, and the like in order to aid the user in sleeping. The present invention however, can be utilized to promote relaxation and sleep by providing aromatherapy fragrances, oils and the like embedded within at least one of a plurality of layers of the invention.

These prior art devices have several known drawbacks. The above discussed devices do not provide for a disposable and scented pad comprising a plurality of layers that include a waterproof layer, a gel layer, fabric layer, and/or sponge layer. In light of the devices disclosed in the prior art, it is submitted that the present invention substantially diverges in design elements from the prior art and consequently it is clear that there is a need in the art for an improvement to existing disposable and/or scented mattress pad devices. In this regard the instant invention substantially fulfills these needs.

SUMMARY OF THE INVENTION

In view of the foregoing disadvantages inherent in the known types of disposable and/or scented pillow pads now present in the prior art, the present invention provides a new scented and disposable pad wherein the same can be utilized for providing convenience for the user when sleeping in bed.

It is therefore an object of the present invention to provide a new and improved disposable and scented pad device that has all of the advantages of the prior art and none of the disadvantages.

It is another object of the present invention to provide a disposable and scented pad having a plurality of layers that include a fabric layer, a gel layer, and a waterproof layer.

It is another object of the present invention to provide a disposable and scented pad, wherein at least one of the plurality of layers is embedded with a scent or fragrance.

Another object of the present invention to provide a disposable and scented pad that can be placed underneath a mattress or overtop of a mattress.

Another object of the present invention is to provide a disposable and scented pad that can be placed between a pillow cover and a pillow.

Yet another object of the present invention is to provide a disposable and scented pad that can promote sleep, relaxation and mood.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
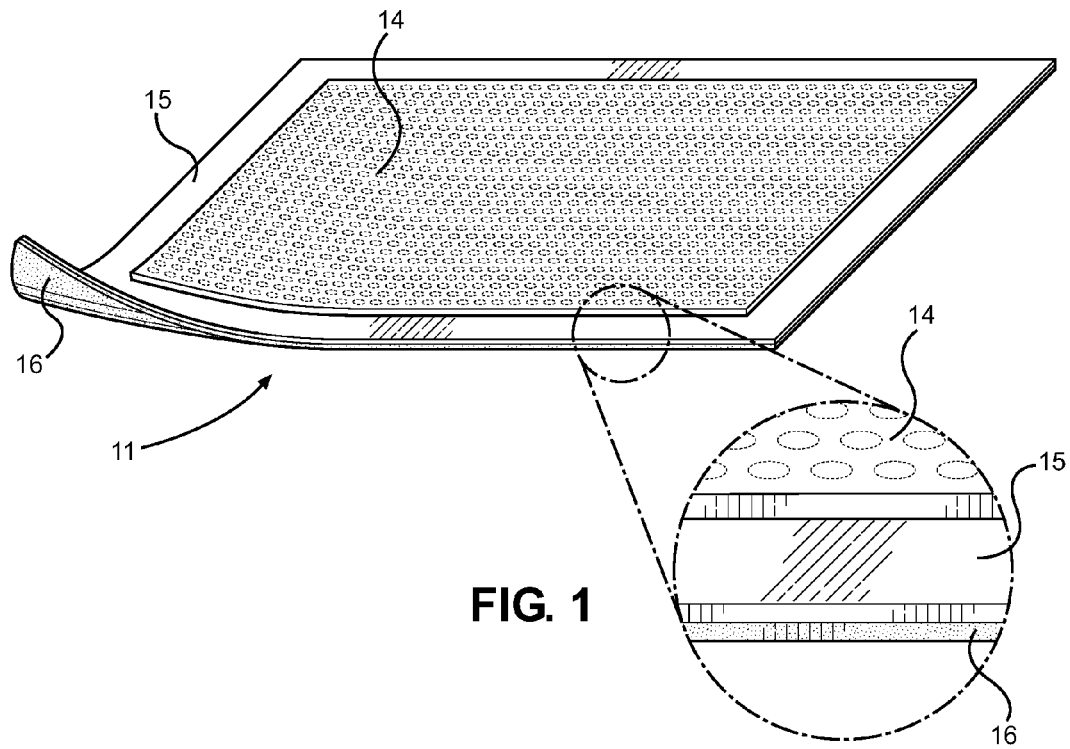
FIG. 1 shows a view of the scented and disposable pillow pad having a plurality of layers.

Reference is made herein to the attached drawings. Like reference numerals are used throughout the drawings to depict like or similar elements of the scented and disposable pad. For the purposes of presenting a brief and clear description of the present invention, the preferred embodiment will be discussed as used for emitting a pleasing scent therefrom in order to promote sleep, relaxation and an increased mood to the user. Further, the invention can be embedded with aromatherapy and/or medicinal scents. The figures are intended for representative purposes only and should not be considered to be limiting in any respect.

Referring now to FIG. 1, there is shown a view of the scented and disposable pad 11 having a plurality of layers. In a preferred embodiment, the disposable pad 11 preferably comprises three layers. The plurality of layers provide a first layer 14, a second layer, and a third layer, wherein the first layer 14 is composed of an absorbent material, the second layer is a gel layer, and third layer is a waterproof layer. At least one of the three layers described can be embedded with a fragrance, deodorizer, scent, essential oil, aromatherapy oil, herbs and/or other suitable scents. These scents are adapted to aid the user with sleeping, relaxation and the improvement of mood. Further, medicinal scents such as menthol, peppermint, tea tree, cardamom, bergamot, lavender and/or other suitable scents.

The first layer 14 comprises an absorbent sheet or can be a fabric layer. The first layer 14 may include a plurality of depressions thereon in order to aid with absorption and/or collection of sweat and/or other bodily fluids. The first layer 14 is preferably rectangular in shape and is substantially planar in structure. The first layer 14 can comprise a soft fabric material such as cotton, paper, polyester, cellucotton, polyacrylate, polypropylene, polyethylene film, and/or other suitable materials. Alternatively, the first layer 14 can comprise a foam or sponge-like material, depending upon the embodiment. The first layer 14 can be embedded with a fragrance, deodorizer, scent, essential oil, aromatherapy oil, herbs and/or other suitable scents in a preferred embodiment. The scented material may be in the form of micro beads embedded within the first layer 14. In alternate embodiments, the second layer and third layer can also be embedded with a fragrance, deodorizer, scent, essential oil, aromatherapy oil, herbs and the like.

The second layer 15 comprises a gel sheet having a substantial thickness in order to provide a padded support for users when resting their body thereon. The second layer 15 is substantially rectangular and is sized similarly to the first layer. The second layer 15 or gel sheet can include, but is not limited to, thermoplastic polyurethanes, polyamides, thermoplastic poly olefins, polyureas, silicone gel, polyol gel, PVC gel, polyorganosiloxane gel, foam gels, NCO-prepolymer gels and/or other suitable gels. The second layer 15 can further be embedded with a fragrance, deodorizer, scent, essential oil, aromatherapy oil, herbs and the like. The second layer 15 can comprise essential oils, aromatherapy oils, spices, menthol, camphor, eucalyptol, botanical and other suitable oils and scents. In a preferred embodiment, the gel layer is embedded with micro beads in order to provide a scent to the gel layer. The micro beads are scented and comprise different fragrances such as lavender, vanilla, chamomile, cinnamon, cotton, sandalwood and other suitable fragrances. However, the micro beads can be embedded into a fabric layer or at least one of the plurality of layers.

The third layer comprises a waterproof sheet having a larger surface area than the first layer 14 and the second layer in order to provide an additional barrier to sweat and/or other bodily fluids that have become absorbed and/or trapped on the first layer 14 via the absorbent sheet. The absorbent sheet can include various materials, including but not limited to polyvinyl chloride, wax, polyester, nylon, acrylic, rayon fibers, polypropylene, and/or other suitable materials. The third layer can further be embedded with a fragrance, deodorizer, scent, essential oil, aromatherapy oil, herbs and the like.

Figure 2:
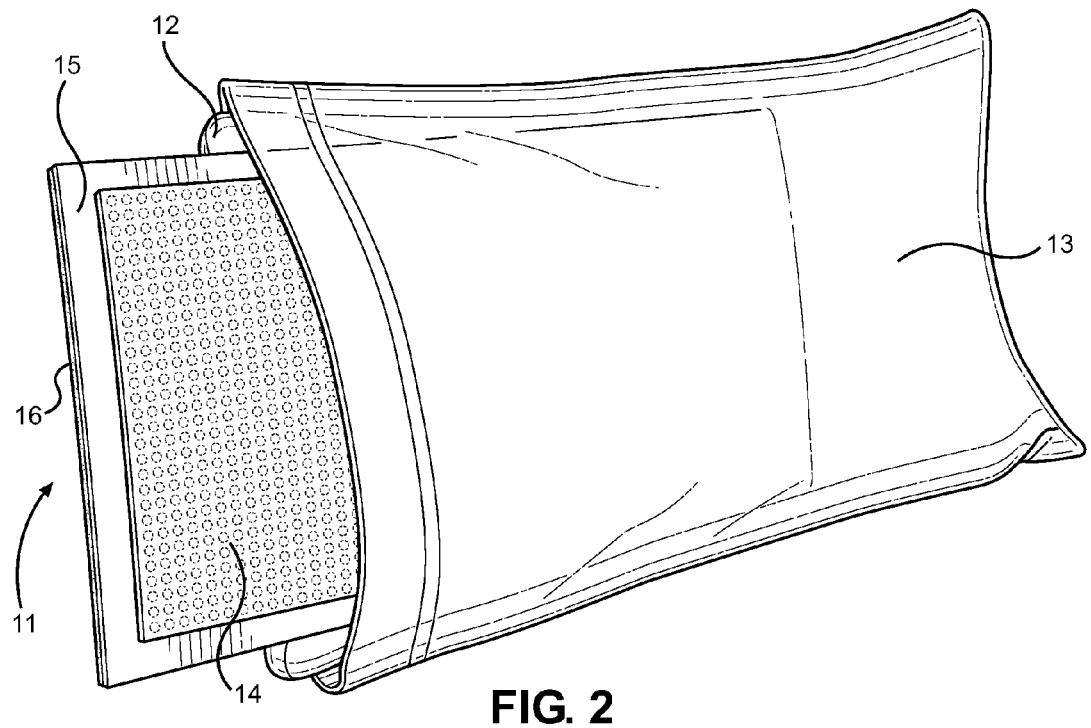
FIG. 2 shows a view of the scented and disposable pillow pad being placed in between a pillow cover and a pillow.

Referring now to FIG. 2, there is shown a view of the scented and disposable pillow pad being placed in between a pillow cover and a pillow. The first layer 14, second layer, and third layer can be affixed to one another via stitching, heat sealing, an adhesive, and/or any other suitable means for adherence such that the layers form one unitary body. The scented and disposable pad 11 can be placed in various areas of a bed in order to emit a pleasing scent therefrom and can further be utilized to trap and absorb sweat and other bodily fluid while lying in bed and/or sleeping. The user can place the scented and disposable pad 11 between a pillow case 13 and a pillow 12, wherein the scented and disposable pad 11 can emit a pleasing scent that can be smelled through the surface of the pillow case 13.

In an alternative embodiment, the scented and disposable pad 11 is unscented and instead provides odor eliminating properties in order to relinquish the scent of sweat and/or other bodily fluids absorbed thereon. The disposable pad 11 can include a sponge or foam sheet having a substantial thickness in order to provide comfort and support to the user's body lying thereon and so as to absorb bodily fluids. Further, the disposable pad includes a waterproof layer for preventing bodily fluids such as sweat, urine and the life from contact the mattress and the bed sheet of the bed to which it is applied. One or more of the layers includes odor eliminating materials or substances for removing foul odors.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pillow assembly, comprising:
a pad including a first layer that comprises an absorbent material, a second layer that comprises a gel material, and a third layer that comprises a waterproof material;
the second layer including scented microbeads embedded therein;
the pad disposed between a pillow and a pillowcase, wherein the first layer is oriented towards the pillowcase.

2. The pillow assembly of claim 1, wherein the first layer is composed of a foam material.

3. The pillow assembly of claim 1, wherein the first layer is composed of a fabric material.

4. The pillow assembly of claim 1, wherein the first layer is composed of a mesh material.

5. The pillow assembly of claim 1, wherein the first layer includes an embedded fragrance.

6. The pillow assembly of claim 1, wherein the gel material is selected from the group consisting of thermoplastic polyurethanes, polyamides, thermoplastic poly olefins, polyureas, silicone gel, polyol gel, PVC gel, polyorganosiloxane gel, foam gels, and NCO-prepolymer gels.

7. The pillow assembly of claim 1, wherein the waterproof material is selected from the group consisting of polyvinyl chloride, wax, polyester, nylon, acrylic, rayon fibers, and polypropylene.

8. The pillow assembly of claim 1, wherein the third layer is larger in surface area than each of the first layer and the second layer.

9. The pillow assembly of claim 1, wherein the third layer includes an embedded fragrance.

* * * * *